(12) United States Patent
Dadourian

(10) Patent No.: US 11,432,855 B2
(45) Date of Patent: Sep. 6, 2022

(54) COMPRESSIVE INTRAMEDULLARY ROD

(71) Applicant: Gregory Haig Dadourian, Rochester, NY (US)

(72) Inventor: Gregory Haig Dadourian, Rochester, NY (US)

( * ) Notice: Subject to any disclaimer, the term of this patent is extended or adjusted under 35 U.S.C. 154(b) by 405 days.

(21) Appl. No.: 16/690,623

(22) Filed: Nov. 21, 2019

(65) Prior Publication Data
US 2020/0197054 A1 Jun. 25, 2020

Related U.S. Application Data

(60) Provisional application No. 62/781,919, filed on Dec. 19, 2018.

(51) Int. Cl.
| *A61B 17/72* | (2006.01) |
| *A61B 17/68* | (2006.01) |
| *A61B 17/00* | (2006.01) |
| *A61B 17/88* | (2006.01) |
| *A61B 17/34* | (2006.01) |

(52) U.S. Cl.
CPC .... *A61B 17/7225* (2013.01); *A61B 17/00234* (2013.01); *A61B 17/683* (2013.01); *A61B 17/7283* (2013.01); *A61B 17/8897* (2013.01); *A61B 17/3421* (2013.01); *A61B 2017/00991* (2013.01); *A61B 2017/349* (2013.01)

(58) Field of Classification Search
CPC . A61B 17/72; A61B 17/7216; A61B 17/7225; A61B 17/7233; A61B 17/7241
USPC .................................................. 606/62–64
See application file for complete search history.

(56) References Cited

U.S. PATENT DOCUMENTS

| 3,709,218 A | 1/1973 | Halloran |
| 4,091,806 A | 5/1978 | Aginsky |
| 4,237,875 A | 12/1980 | Termanini |
| (Continued) | | |

FOREIGN PATENT DOCUMENTS

IN 201611042557 A 6/2018

OTHER PUBLICATIONS

International search report issued in corresponding international application No. PCT/US2019/062575 dated Jan. 15, 2020.

*Primary Examiner* — Eduardo C Robert
*Assistant Examiner* — Christina Negrellirodriguez
(74) *Attorney, Agent, or Firm* — Young Basile Hanlon & MacFarlane, P.C.

(57) ABSTRACT

A compressive intramedullary rod includes first and second concentric shafts configured to engage with each other in a telescopic manner along a longitudinal axis, through a screw mechanism integrated in the first concentric shaft. The screw mechanism includes a bolt in an upper portion for mounting onto the first concentric shaft, and an externally threaded rod in a lower portion for engaging with an internally threaded first channel of the second concentric shaft. The second concentric shaft includes a second channel extending along corresponding length, and the externally threaded rod portion includes a third channel extending along corresponding length. Further, the second channel fully aligns with the third channel, when first and second concentric shafts engage in a telescopic manner upon rotation of the screw mechanism. The first and second concentric shafts include first and second set of guide holes for coupling to proximal and distal fragments of bone.

20 Claims, 14 Drawing Sheets

(56) References Cited

U.S. PATENT DOCUMENTS

| | | |
|---|---|---|
| 4,262,665 A | 4/1981 | Roalstad et al. |
| 5,352,228 A | 10/1994 | Kummer et al. |
| 5,704,939 A | 1/1998 | Justin |
| 6,524,313 B1 | 2/2003 | Fassier et al. |
| 6,692,530 B2 | 2/2004 | Doubler et al. |
| 6,755,862 B2 | 6/2004 | Keynan |
| 7,753,915 B1 | 7/2010 | Eksler et al. |
| 8,449,543 B2 | 5/2013 | Pool et al. |
| 8,777,947 B2 | 7/2014 | Zahrly et al. |
| 8,876,821 B2 | 11/2014 | Kinmon |
| 9,381,052 B2 | 7/2016 | Ziran |
| 9,474,556 B2 | 10/2016 | Diao et al. |
| 9,730,739 B2 | 8/2017 | Taylor et al. |
| 9,757,169 B2 | 9/2017 | Boraiah |
| 9,814,499 B2 | 11/2017 | Buscaglia et al. |
| 2012/0209265 A1* | 8/2012 | Pool .................... A61B 17/921 606/62 |
| 2014/0243825 A1 | 8/2014 | Yapp et al. |
| 2015/0327902 A1 | 11/2015 | Eekhoff et al. |

* cited by examiner

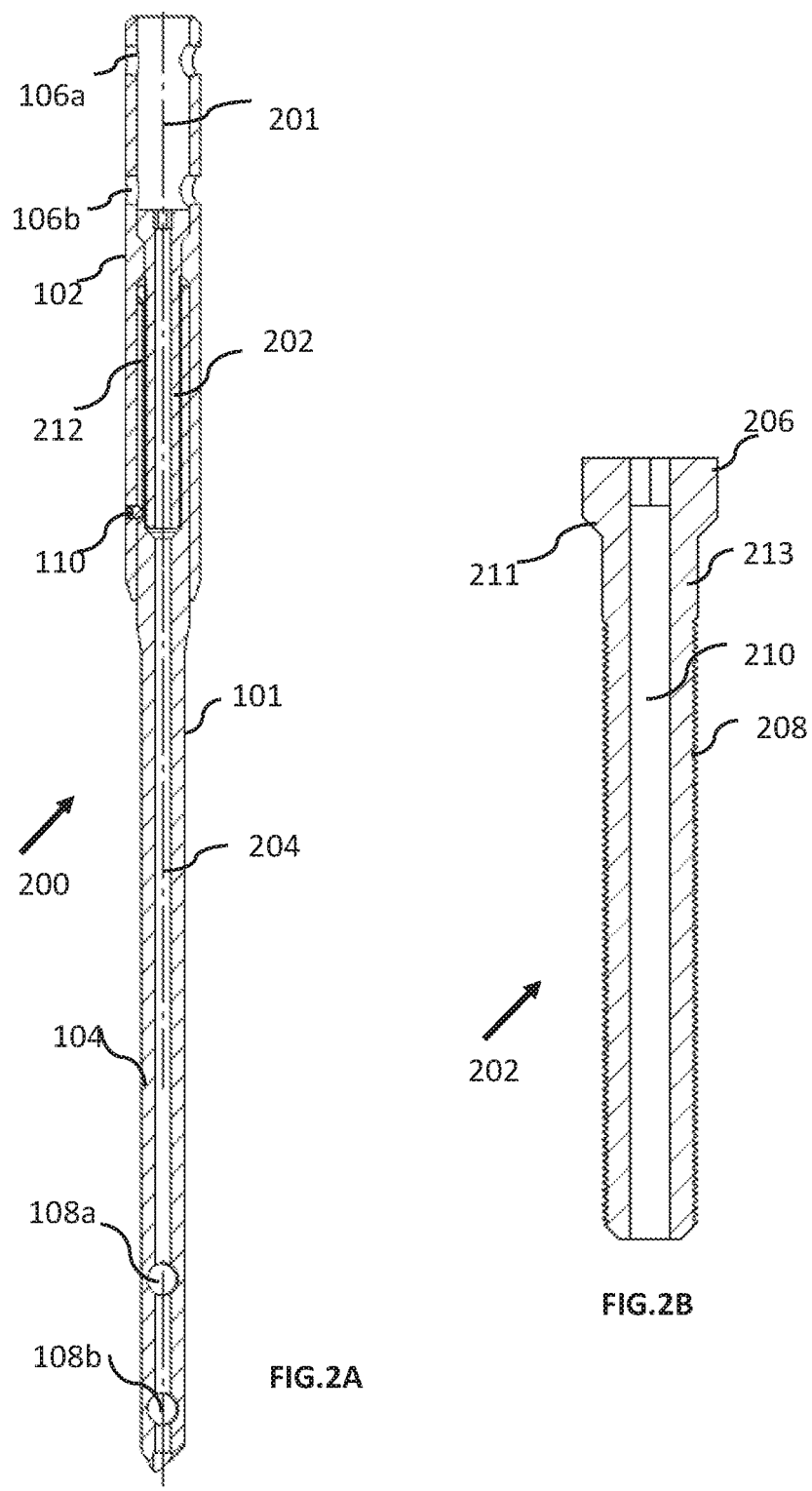

COMPRESSIVE INTRAMEDULLARY ROD

TECHNICAL FIELD

The present disclosure relates generally to a compressive intramedullary rod, and more specifically to an intramedullary rod that allows for minimally invasive fracture fixation, and compression of breaks located in long bones.

BACKGROUND

In the field of medical science, there are two main types of fracture healing: direct (primary) and indirect (secondary). The direct healing requires rigid and stable conditions and anatomically corrects alignment of the bone fragments. This is not often achieved naturally because both halves of the fracture must be in perfect contact. In direct healing, the bone can be remodeled through the work of osteoclasts and osteoblasts, whereas in indirect healing, the bone can be remodeled with the use of a periosteal callus.

Contrastingly, there are three main phases that occur in indirect healing. The initial phase, the inflammatory response, occurs within 72 hours after injury. During this phase, growth factors and other cytokines are released and influence cell migration, proliferation, and differentiation. In addition, they recruit fibroblasts, osteoprogenitor cells, and mesenchymal progenitor cells. Mesenchymal progenitor cells can differentiate into chondrocytes or osteoblasts depending on mechanical forces at the time of differentiation. The process of removing damaged tissue begins during the initial phase as well. The second phase, the reparative response phase, occurs 2 days to 2 weeks after injury. In this phase, new vasculature begins to form and differentiated mesenchymal cells form cartilage, bone, or fibrous tissue at the site of injury. The last phase, bone healing and remodeling, can last as long as up to seven years after initial injury. On a microscopic level, the changes in bone remodeling are governed by osteocytes and osteoprogenitor cells, which are both mechano-sensors. Also, it has been researched, that sufficient contact pressure and a small fracture gap contribute to an improved healing rate, and increased periosteal bone formation.

There exist two general approaches to surgically repairing the humerus (the long bone in the arm that runs from the shoulder to the elbow) through indirect healing, plate fixation and intramedullary (IM) nailing. The "plate fixation" method, utilizes a large metal plate as a bone implant, such that the metal plate is screwed directly to the bone along the fracture site, requiring an incision of similar length to the implant. The plate allows for direct compression of the bone fragments and acts as an internal split, resulting in absolute stability of the fracture site. While this is good, plate fixation brings a list of risks as well. Firstly, there are major nerves (i.e. axillary, radial, and ulnar) that wrap around the humerus and can cause pain or paralysis if damaged. Secondly, there is a 32% increase in infection rate due to the size of the incision.

IM nailing involves making a minimally invasive incision along the shoulder, reaming out the canal of the bone, and inserting a bone implant such as a cannulated rod down the canal. Screws are used to fixate the rod at each end of the bone to prevent the fracture from shortening and rotating, as well as hold the rod in place. While minimally invasive approaches are much preferred by surgeons, they still pose their own set of risks. These include a decreased range of shoulder motion due to insertion of the rod through the rotator cuff, and higher rates of non-union due to the rod's inability to compress the fracture site.

Therefore, in light of the foregoing discussion, there exists a need for a bone implant that repairs the bone effectively through direct healing, and that overcomes the limitations of existing bone implants.

SUMMARY

In one aspect of the present disclosure, there is provided a compressive intramedullary rod that comprises first and second concentric shafts configured to engage with each other in a telescopic manner along a longitudinal axis, through a screw mechanism integrated in the first concentric shaft. The screw mechanism comprises a bolt in an upper portion for mounting onto the first concentric shaft, and an externally threaded rod in a lower portion for engaging with an internally threaded first channel of the second concentric shaft and the second concentric shaft includes a second channel extending along corresponding length. The externally threaded rod portion includes a third channel extending along corresponding length, wherein the second channel fully aligns with the third channel, when the first and second concentric shafts engage in a telescopic manner upon rotation of the screw mechanism. The first concentric shaft includes a first set of guide holes disposed in a spaced apart relationship with each other, such that first concentric shaft is configured to be fixed to a proximal fragment of a bone through the first set of guide holes. The second concentric shaft includes a second set of guide holes disposed in a spaced apart relationship with each other, such that second concentric shaft is configured to be fixed to a distal fragment of a bone through the second set of guide holes, wherein first and second set of guide holes are inclined at a differential angle with respect to each other. The differential angle is determined based on an anatomy of the bone to be healed using the compressive intramedullary rod.

In another aspect of the present disclosure, there is provided a system for fixing a bone fracture in a minimally invasive manner, and for compressing breaks located in a long bone. The system includes a compressive intramedullary rod that comprises first and second concentric shafts configured to engage with each other in a telescopic manner along a longitudinal axis, through a screw mechanism integrated in the first concentric shaft. The screw mechanism comprises a bolt in an upper portion for mounting onto the first concentric shaft, and an externally threaded rod in a lower portion for engaging with an internally threaded first channel of the second concentric shaft, and the second concentric shaft includes a second channel extending along corresponding length. The externally threaded rod portion includes a third channel extending along corresponding length, wherein the second channel fully aligns with the third channel, when the first and second concentric shafts engage in a telescopic manner upon rotation of the screw mechanism. The first concentric shaft includes a first set of guide holes disposed in a spaced apart relationship with each other, such that the first concentric shaft is configured to be fixed to a proximal fragment of a bone through the first set of guide holes, and the second concentric shaft includes a second set of guide holes disposed in a spaced apart relationship with each other, such that the second concentric shaft is configured to be fixed to a distal fragment of a bone through the second set of guide holes. The first and second set of guide holes are inclined at a differential angle with respect to each other, the differential angle being determined based on an anatomy of the bone to be healed using the compressive intramedullary rod. The system further includes a deployment system for implanting the compressive intramedullary rod in the bone. The deployment system includes a fixation pin having a trocar tip, and a hole that is located adjacent to the trocar trip and is in a direction perpendicular to a primary axis of the fixation pin. The fixation pin is configured to insert through a guide hole of the first concentric shaft, to hold the proximal fragment of the bone to a proximal end of the first concentric shaft, while one or more standard screws through the second set of guide holes hold a distal end of the second concentric shaft to the distal fragment of the bone. The deployment system further includes a hex key configured to insert into the hole of the fixation pin for creating compression between the proximal end of the first concentric shaft and the distal end of the second concentric shaft upon turning, while the screw mechanism is engaged, a first arm coupled to the hex key for facilitating implant attachment, and a second arm coupled to the hex key for facilitating alignment of the hole of the fixation pin.

In yet another aspect of the present disclosure, there is provided a deployment system for implanting a compressive intramedullary rod in a bone during a fracture repairing process of the bone. The compressive intramedullary rod includes first and second concentric shafts configured to engage with each other in a telescopic manner along a longitudinal axis, through a screw mechanism integrated in the first concentric shaft. The deployment system includes a fixation pin having a trocar tip, and a hole that is located adjacent to the trocar trip and in a direction perpendicular to a primary axis of the fixation pin. The fixation pin is configured to insert through a guide hole of the first concentric shaft, to hold a proximal fragment of the bone to a proximal end of the first concentric shaft, while one or more standard screws hold a distal end of the second concentric shaft to a distal fragment of the bone. The deployment system further includes a hex key configured to insert into the hole of the fixation pin for creating compression between the proximal end of the first concentric shaft and the distal end of the second concentric shaft upon turning, while the screw mechanism is engaged.

In yet another aspect of the present disclosure, there is provided a method for implanting a compressive intramedullary rod in a bone during a fracture repairing process of the bone using a deployment device. The compressive intramedullary rod includes proximal and distal concentric shafts configured to engage with each other in a telescopic manner along a longitudinal axis, through a screw mechanism integrated in the first concentric shaft. The proximal and distal concentric shafts includes proximal and distal holes, the deployment device having a fixation pin that has a trocar tip, and a key hole that is located adjacent to the trocar trip, and a hex key configured to insert into the key hole of the fixation pin for creating compression between the proximal end of the proximal concentric shaft and the distal end of the distal concentric shaft. The method includes drilling a hole in the bone, positioning a guide wire in the fractured bone such that the guide wire stretches from an opening by incision to a distal most surface in a intramedullary cavity, attaching a compressive intramedullary rod to a deployment arm of the deployment device, pushing the compressive intramedullary rod into the fractured bone along the path of the guide wire, removing the guide wire, attaching distal concentric shaft to the bone by implanting distal fixation screws through distal holes, inserting the fixation pin in one of the proximal holes, inserting the hex key through the key hole in the deployment arm and the fixation pin, such that the hex key interfaces with the screw mechanism, tightening the screw mechanism through the hex key, causing compression of the fractured bone, removing the hex key once compression is achieved, and a first proximal fixation screw is implanted through first proximal hole, and removing the fixation pin, and implanting the second proximal fixation screw through second proximal hole.

It will be appreciated that features of the present invention are susceptible to being combined in various combinations without departing from the scope of the present invention as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein:

FIG. 2A is a cross-sectional view of the compressive intramedullary rod along a corresponding telescopic axis, in accordance with an embodiment of present disclosure;

FIG. 2B illustrates an enlarged view of a screw mechanism of the compressive intramedullary rod, in accordance with an embodiment of present disclosure;

FIGS. 5A-5L illustrate a method for implanting a compressive intramedullary rod in a bone during repairing a fracture of the bone using a deployment device, in accordance with an embodiment of present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

Figure 1:
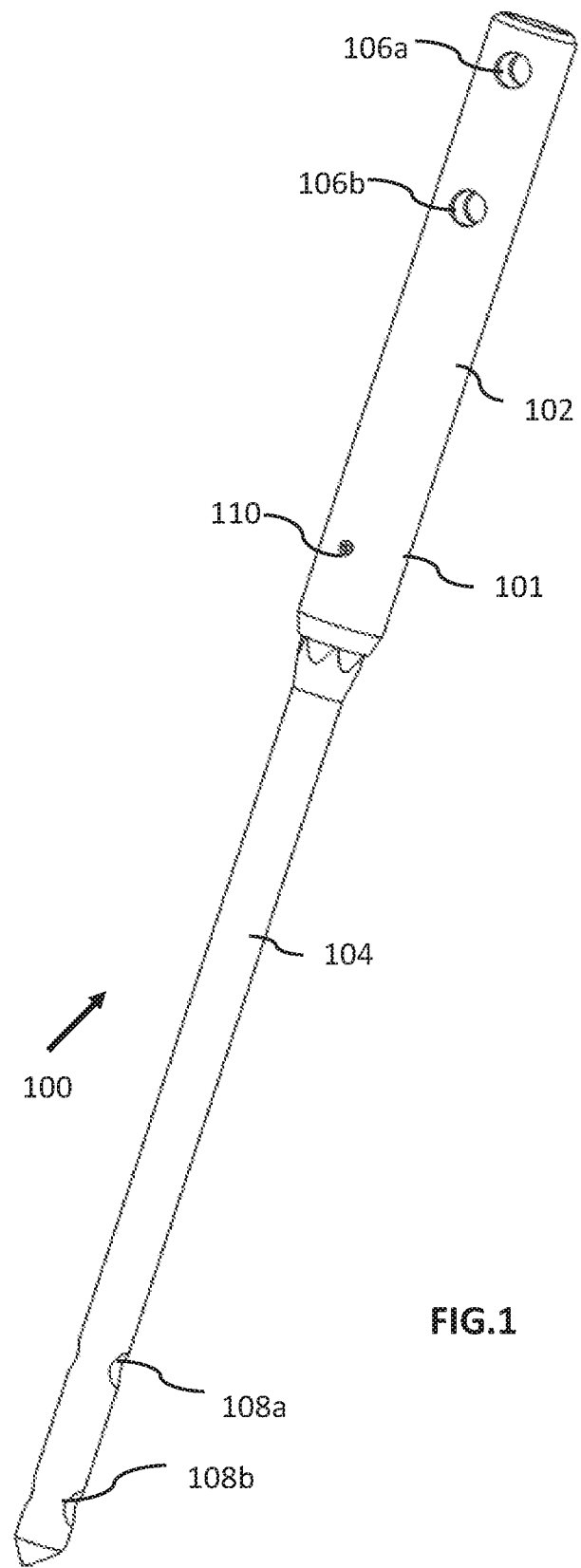
FIG. 1 is a front perspective view of a compressive intramedullary rod, in accordance with an embodiment of the present disclosure.

FIG. 1 is a front perspective view 100 of a compressive intramedullary rod 101, in accordance with an embodiment of the present disclosure.

The primary use of the compressive intramedullary rod 101 is in orthopedic trauma surgery and join arthroplasty, where it is intended for use in long bones, when a fracture occurs in the metaphysis or diaphysis. The compressive intramedullary rod 101 is designed to fixate and compress the fracture in order for healing to take place. The compressive intramedullary rod 101 is designed such that the mechanical interior can be used with varying external geometries, thus maximizing the devices possible usage (long bones of different sizes, as well as patients of varying sizes).

The compressive intramedullary rod 101 includes two concentric shafts, i.e. a proximal shaft 102 and a distal shaft 104 connected to each other in a telescopic manner. In an embodiment of the present disclosure, the distal shaft 104 is the larger of the two concentric shafts. The extended length of the distal shaft 104 enables more realistic modelling of a humeral nail.

In an embodiment of the present disclosure, the concentric shafts 102 and 104 telescope along a central axis in relation to each other. The two concentric shafts 102 and 104, are mated about one surface, such that the outer surface of the smaller shaft 104 and the inner surface of the larger shaft 102 are in contact with each other.

In an embodiment of the present disclosure, the bottom portion of the proximal shaft 102 extends outside (visible to the user), and the top portion of the distal shaft 104 extends inside (not visible to the user) the proximal shaft 102. However, it would be apparent to one of ordinary skill in the art, that in some variants, the bottom portion of the distal shaft 104 may extend inside (not visible to the user), and the top portion of the proximal shaft 102 may extend outside (visible to the user).

The proximal shaft 102 includes first and second screw holes 106a and 106b, (hereinafter collectively referred to as proximal screw holes 106), and the distal shaft 104 includes third and fourth screw holes 108a and 108b, (hereinafter collectively referred to as distal screw holes 108). Although, two proximal and two screw holes 106 and 108 are shown herein for the sake of brevity, it would be apparent to one of ordinary skill in the art, that the compressive intramedullary rod 101 may include more than two proximal and distal screw holes 106 and 108.

In an embodiment of the present disclosure, the proximal and distal screw holes 106 and 108, are cut into respective proximal and distal shafts 102 and 104 in a direction perpendicular to the telescopic axis for attaching the rod 101 with corresponding bone. In an embodiment of the present disclosure, the proximal and distal screw holes 106 and 108 may be disposed at a differential angle with respect to each other. The differential angle may be set based on an anatomy of the humerus, i.e. the long bone in the arm that runs from the shoulder to the elbow. There are nerve groups in the humerus that need to be avoided during nailing, so the positioning of the screws depends on the position in the humerus. Examples of the differential angle include, but are not limited to 30, 90, and 150 degrees. It would be apparent to one of ordinary skill in the art, that any differential angle is achievable by adjusting manufacturing characteristics of the holes in angular relation to the hexagonal cross section.

In an embodiment of the present disclosure, the proximal shaft 102 includes a small stud 110. The small stud 110 may be embedded on an internal surface of the proximal end of the proximal shaft 102. The stud 110 has been further illustrated with reference to FIG. 2A.

It would be apparent to one of ordinary skill in the art, that the proximal and distal shafts 102 and 104 may have different thicknesses, as well as different lengths and screw hole patterns as is determined by the anatomy of the long bone to be treated/healed.

FIG. 2A is a cross-sectional view 200 of the compressive intramedullary rod 101 along a corresponding telescopic axis 201, in accordance with an embodiment of present disclosure. The proximal shaft 102 includes an externally threaded screw mechanism 202 mounted thereon, for engaging with an internally threaded channel (not shown) of the distal shaft 104, such that as the screw 202 is rotated, the proximal and distal shafts 102 and 104 move in a telescopic manner. The distal shaft 104 further includes a first channel 204 extending along a longitudinal length therein. The cross-sectional view 200 further depicts that the proximal and distal screw holes 106 and 108 are disposed perpendicular to each other.

An enlarged view of the screw mechanism 202 has been described in detail with reference to FIG. 2B. The screw mechanism 202 includes a bolt 206 in an upper portion for mounting onto the proximal shaft 102, such that the bolt 206 fits to the proximal shaft 102 via a 45 degree beveled surface 211. The screw mechanism 202 further includes a rod 208 that includes a second channel 210 that completely aligns with the first channel 204 of the distal shaft 104, while the external threads of the rod 208 enable engaging of the proximal and distal shafts 102 and 104 in a telescopic manner.

It would be apparent to one of ordinary skill in the art, that the screw mechanism 202 may have a bolt and rod interface, other than the prescribed bolt and rod interface, but the functionality is such that the bolt 206 braces itself against the proximal shaft 102, such that it can rotate freely.

In an embodiment of the present disclosure, the alignment of the first and second channels 204 and 210 provides a clear passage for a guide wire that feeds into a patient's fractured humerus through the screw mechanism 202 during the implantation process. Due to the presence of the second channel 210, the screw 202 may be hereinafter referred to a cannulated screw. Utilization of the thickest screw reduces the chances of failure in bending. Cannulation of the screw has a small effect in the reduction of bending strength, so a cannula can be added to the screw to eliminate assembly during surgery and save time.

Referring back to FIG. 2A, it may be noted that due to the cannulation, the screw mechanism 202 may be integrated with the compressive intramedullary rod 101 at the onset, as compared to existing systems, where the screw mechanism 202 is assembled with the rod 101, after the guide wire is used to align the distal shaft 104 for implantation.

In an embodiment of the present disclosure, the screw mechanism 202 may be hereinafter referred to as a compressive element of the compressive intramedullary rod 101 as it pulls the proximal and distal shafts 102 and 104 together to create compression of a bone, once the bone fragments have been fixed to the proximal and distal shafts 102 and 104 via screw holes 106 and 108, respectively. The compressive element of the rod 101 can be used to improve on general fixation and induce faster healing of the bone, as the controlled compression of the fracture site promotes faster and stronger bone healing, which leads to improved patient recovery. The compressive feature of the screw mechanism 202 may be useful in joint arthroplasty, where the connection of the bone to the joint could utilize the compression mechanism in a similar fashion to the proximal bone fragment.

In another embodiment of the present disclosure, the stud 110 provided on an internal surface of the proximal shaft 102 fits into a groove 212 etched into an outer surface of the proximal end of the distal shaft 104 such that the groove 212 is parallel to the telescoping axis 201 of the compressive intramedullary rod 101. The combination of the stud 110 and groove 212 prevents the proximal and distal shafts 102 and 104 from being separated once assembled. In the interest of surgical practice, the proximal and distal shafts 102 and 104, should not be able to dissociate during the surgical implantation or surgical removal. The stud 110 prevents the proximal and distal shafts 102 and 104 from coming apart in the event if the screw 202 is removed. It is essentially a fail-safe for rod removal if the screw 202 breaks.

Figures 3A, 3B:
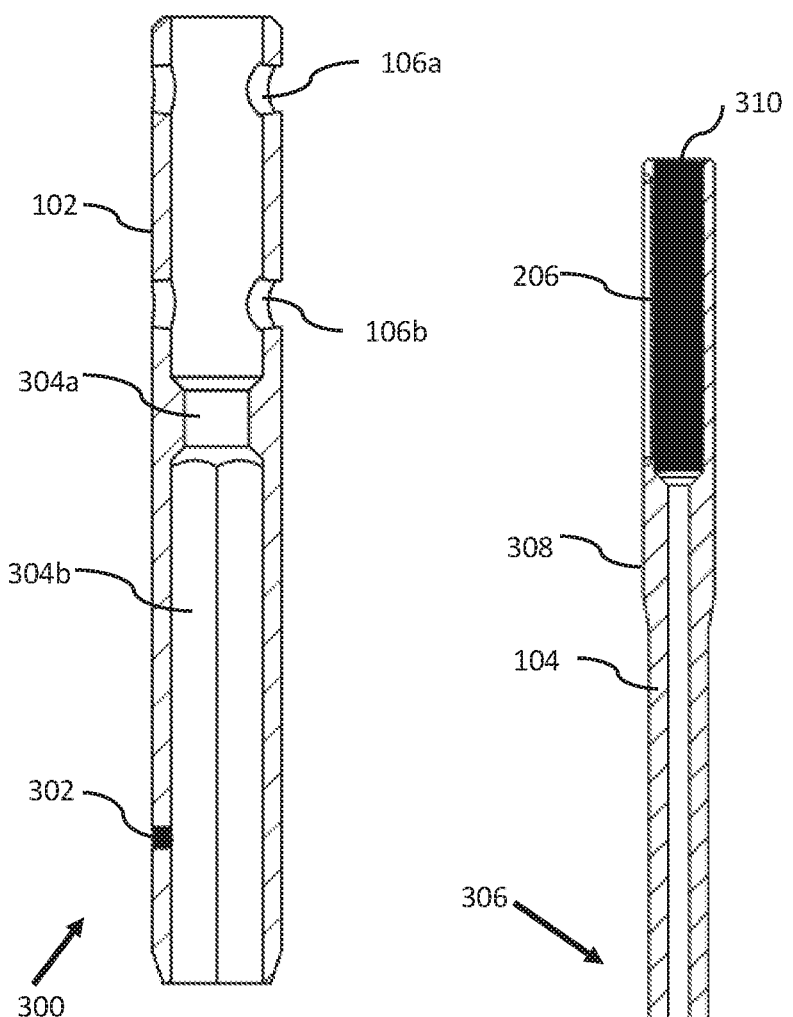
FIG. 3A illustrates a cross-sectional view of a proximal shaft of the compressive intramedullary rod, in accordance with an embodiment of present disclosure.
FIG. 3B illustrates a cross-sectional view of a distal shaft of the compressive intramedullary rod, in accordance with an embodiment of present disclosure.

FIG. 3A illustrates a cross-sectional view 300 of the proximal shaft 102, in accordance with an embodiment of the present disclosure.

The cross-sectional view 300 illustrate the first and second proximal holes 106a and 106b, an insertion point 302 of the stud 110 (not shown), a cylindrical surface 304a that mates with a surface of the screw mechanism 202 (see, FIG. 2B), and a hexagonal cross-section face 304b.

FIG. 3B illustrates a cross-sectional view 306 of the distal shaft 104, in accordance with an embodiment of the present disclosure. The cross-sectional view 306 illustrate the distal holes 108a and 108b, a hexagonal cross section face 308, as well as an internally threaded channel 310 that engages with an externally threaded portion of the screw mechanism 202 of FIG. 2B. In an embodiment of the present disclosure, the hexagonal cross section face 308 prevents the proximal shaft 102 (not shown) and distal shaft 104 from rotating about each other, while still maintaining high resistance to bending. After a surgical procedure is completed, sustained torsional rigidity between the proximal and distal shafts 102 (not shown) and 104 is important to uphold desirable healing conditions. The nature of the concentric shafts 102 and 104 is designed to maintain composite bending throughout the compressive axis of the device 101 while the internal cross sections prevent the proximal and distal shafts 102 (not shown) and 104 from separating.

Figure 4:
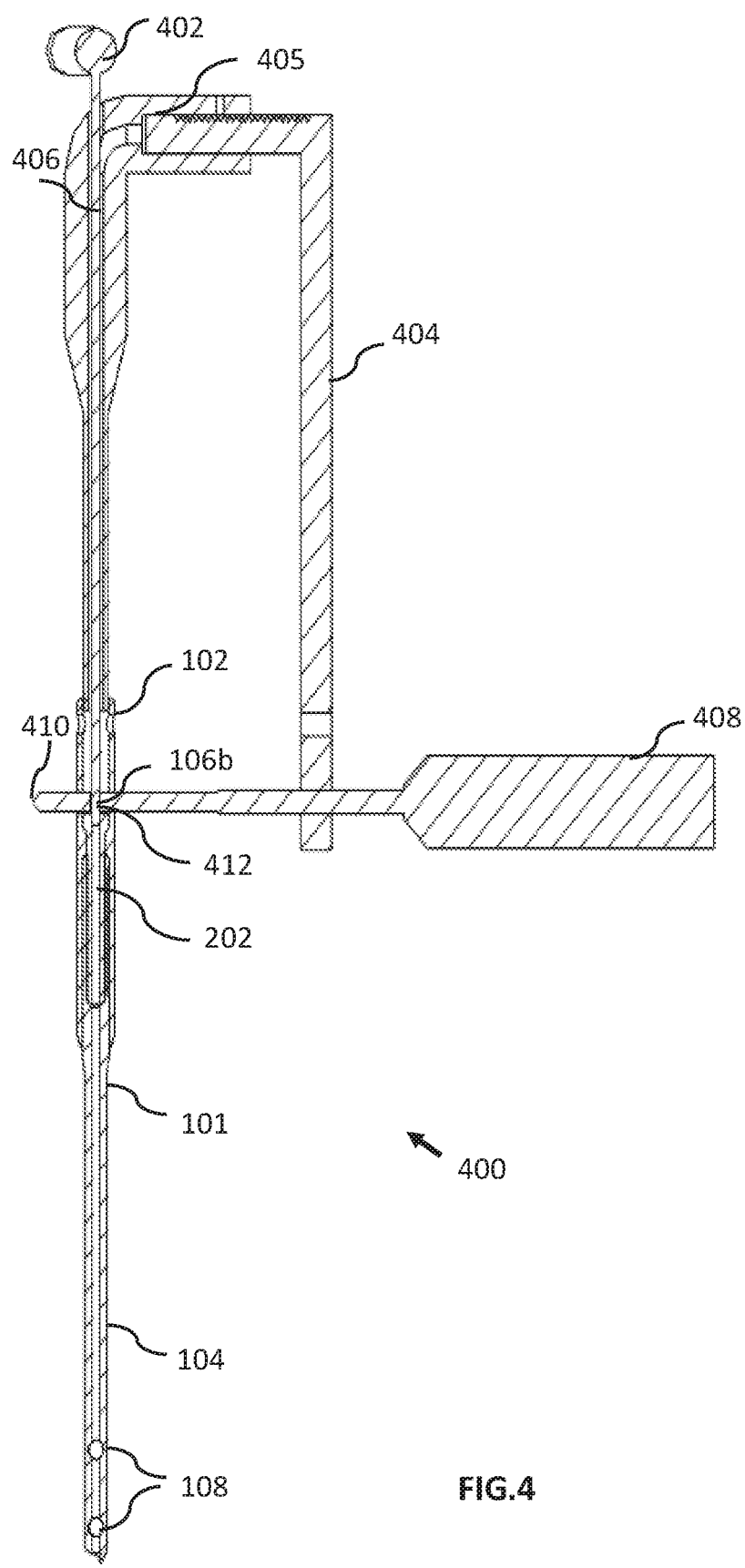
FIG. 4 illustrate a deployment system for the compressive intramedullary rod, in accordance with an embodiment of present disclosure.

FIG. 4 illustrates a deployment system 400 for deploying the compressive intramedullary rod 101 for fixing bone fracture, in accordance with an embodiment of the present disclosure. The deployment system 400 is designed to implant the compressive intramedullary rod 101 and guide the drilling process, and also maintain the fixation of the device 101 on the proximal side of the fracture while the screw mechanism 202 is engaged and simple screws may maintain fixation on the distal end. The deployment system 400 includes a hex key 402, an arm 404 for implant attachment, another arm 406 for hole alignment, a crossbar connection 405 between the arms 404 and 406, and a fixation pin 408.

The fixation pin 408 has a trocar shaped tip 410 and a small hole 412 located close to the trocar tip 410. The hole 412 is perpendicular to a primary axis of the fixation pin 408. In an embodiment of the present disclosure, the fixation pin 408 is configured to insert through a guide hole 106b of the proximal shaft 102, to hold a proximal fragment of the bone to a proximal end of the proximal shaft 102, while one or more standard screws through the second set of guide holes 108 hold a distal end of the distal shaft 104 to the distal fragment of the bone. The fixation pin 408 mates the proximal bone fragment to a proximal end of the rod 101 (after the guide hole has been drilled through corresponding bone). Further, the hex key 402 is configured to insert into the hole 412 of the fixation pin 408 for creating compression between the proximal end of the proximal shaft 102 and the distal end of the distal shaft 104 upon turning, while the screw mechanism 202 is engaged. The hex key 402 may be pushed through the hole 412 and into the screw mechanism 202. It may be noted that the thicker the hex key 402 is, the stronger the key's resistance to torsion, and less twist would be prevalent in the hex key 402 when tightening the rod 101. Also, the shaft of the fixation pin 408 has a square cross section so that the orientation of the fixation pin 408 can be maintained during the procedure.

It would be apparent to one of ordinary skill in the art, that the deployment system 400 may have a different design, based on the design of the compressive intramedullary rod 101.

Figures 5A, 5B:
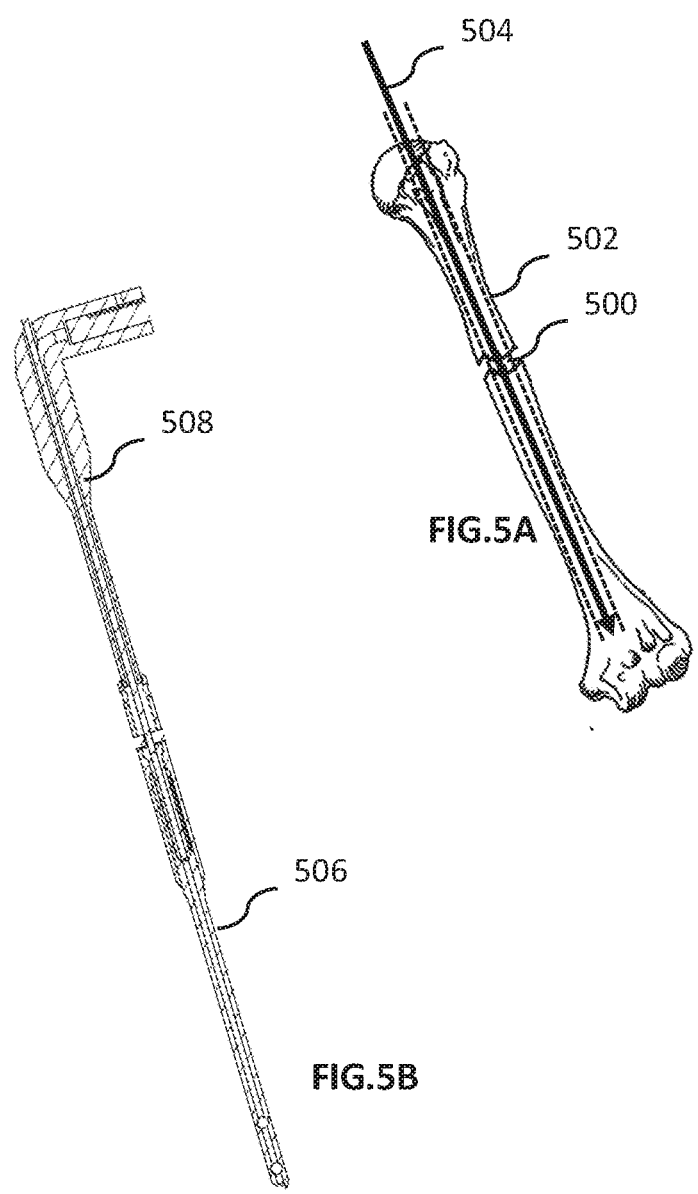

FIG. 5A illustrates drilling a hole in the bone 502, and then positioning a guide wire 504 in the fractured bone 502 such that the guide wire 504 stretches from an opening by incision to a distal most surface in an intramedullary cavity of the bone 502.

FIG. 5B illustrates attaching a compressive intramedullary rod 506 (similar to the one explained with reference to FIG. 1) to a deployment arm 508 of the deployment device (similar to the one explained with reference to FIG. 4).

Figure 5C:
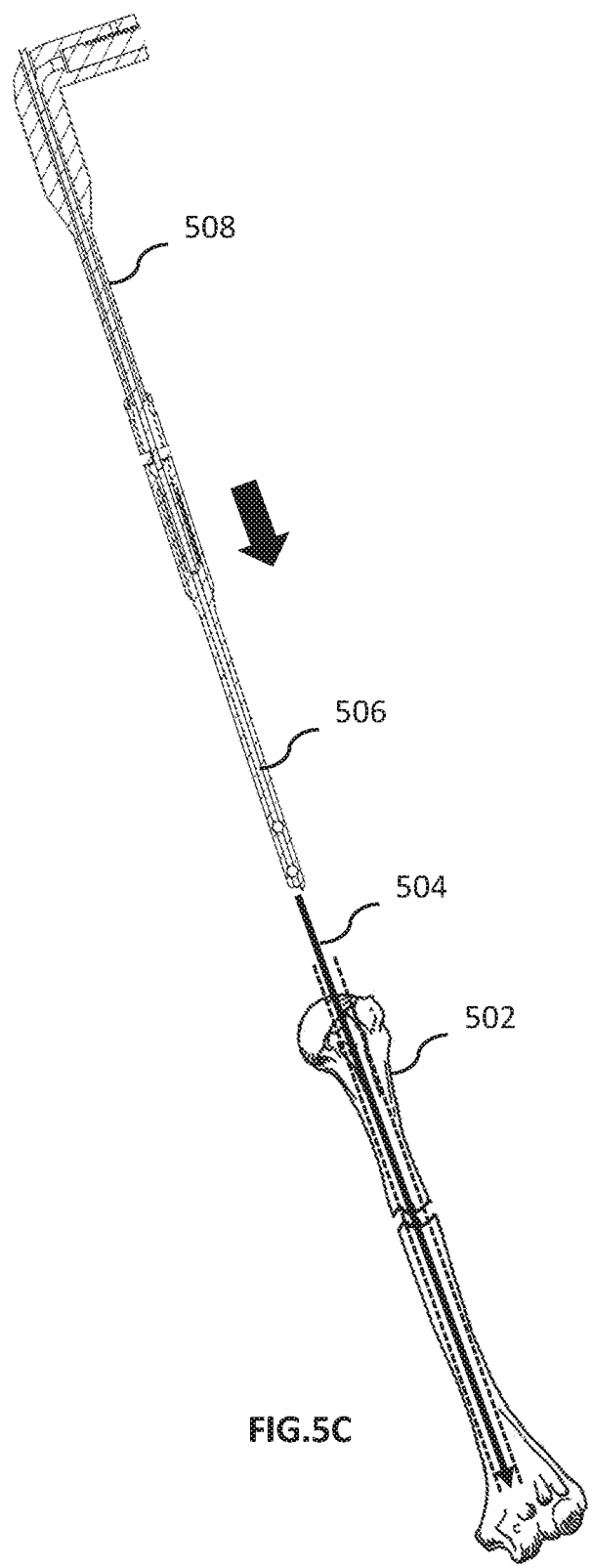
Figure 5D:
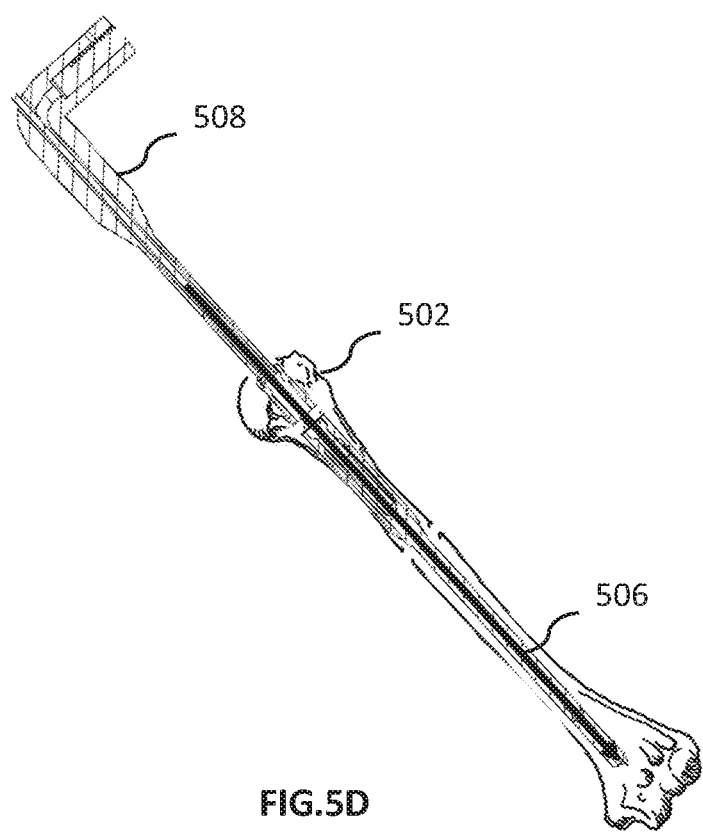

FIGS. 5C and 5D illustrate pushing the compressive intramedullary rod 506 into the fractured bone 502 along the path of the guide wire 504.

Figure 5E:
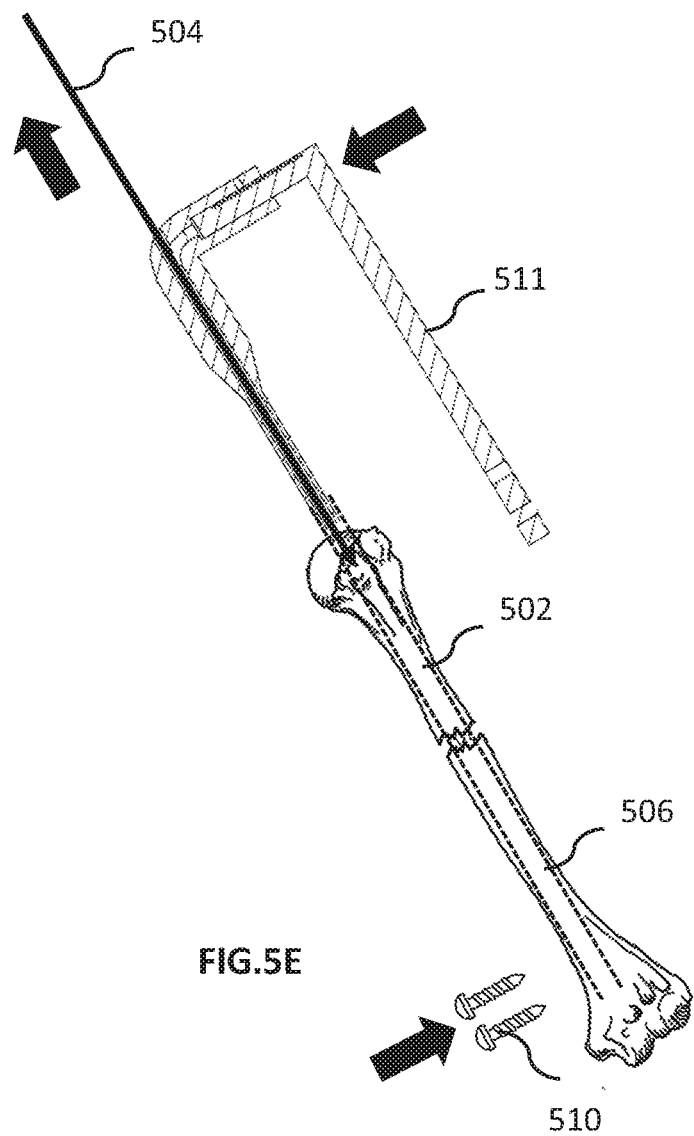

FIG. 5E illustrates removing the guide wire 504 and attaching an arm 511 once the compressive intramedullary rod 506 is completely pushed into the fractured bone 502 and also implanting distal fixation screws 510 into distal holes (not shown) of a distal concentric shaft of the compressive intramedullary rod 506 so as to attach the distal concentric shaft to the bone 502.

Figure 5F:
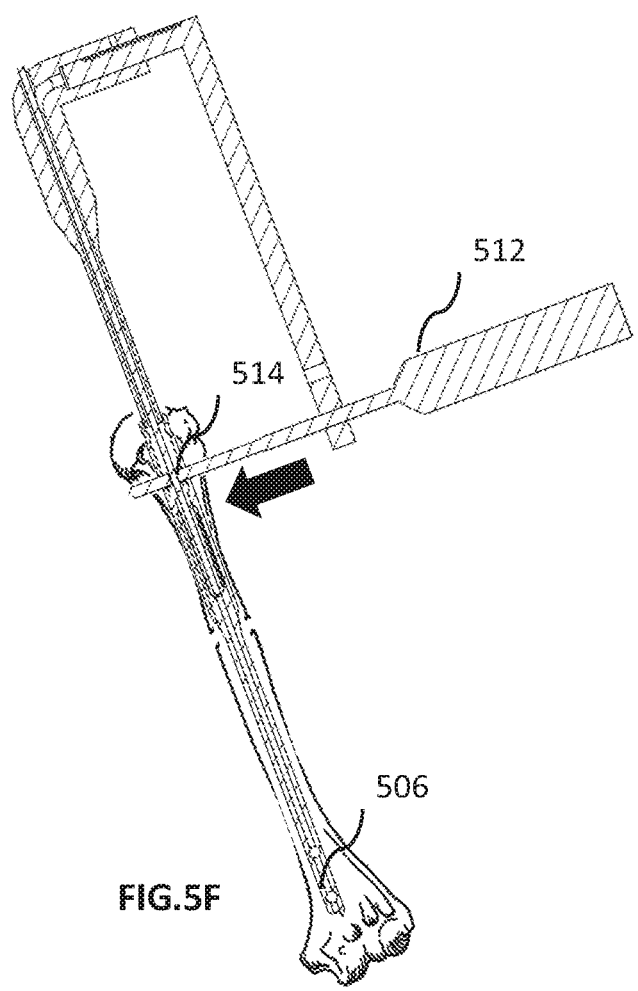

FIG. 5F illustrates inserting a fixation pin 512 in one of the proximal holes 514 of a proximal concentric shaft of the compressive intramedullary rod 506.

Figure 5G:
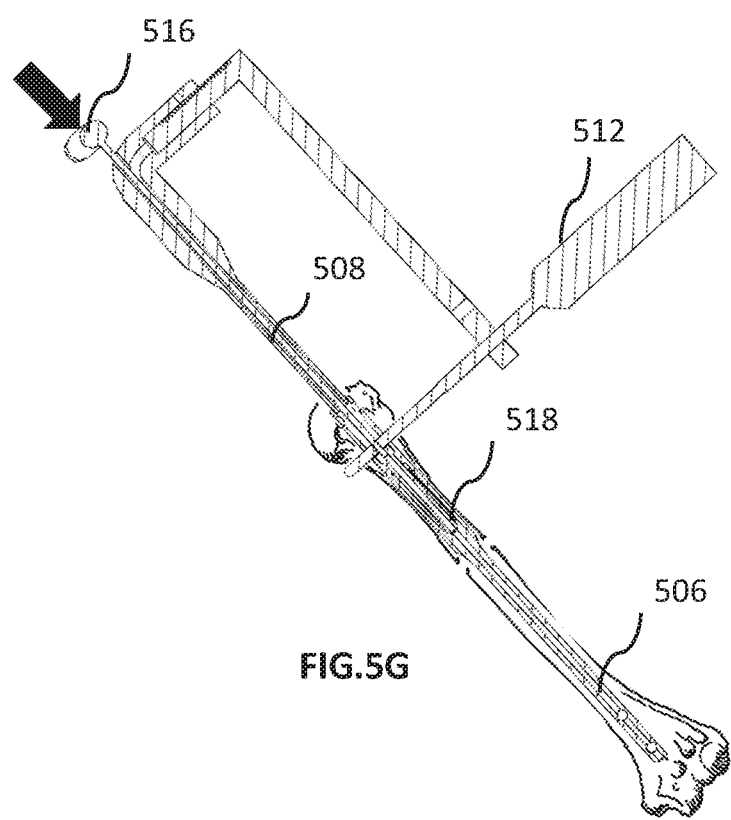

FIG. 5G illustrates inserting a hex key 516 through a key hole in the deployment arm 508 and the fixation pin 512, such that the hex key 516 interfaces with a screw mechanism 518 of the compressive intramedullary rod 506.

Figure 5H:
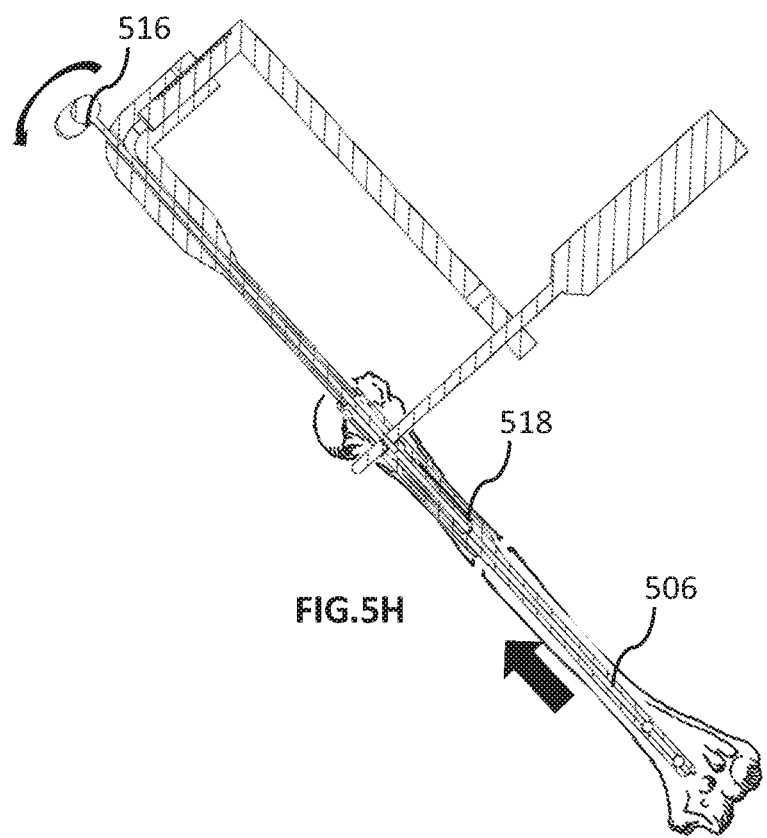
Figure 51:
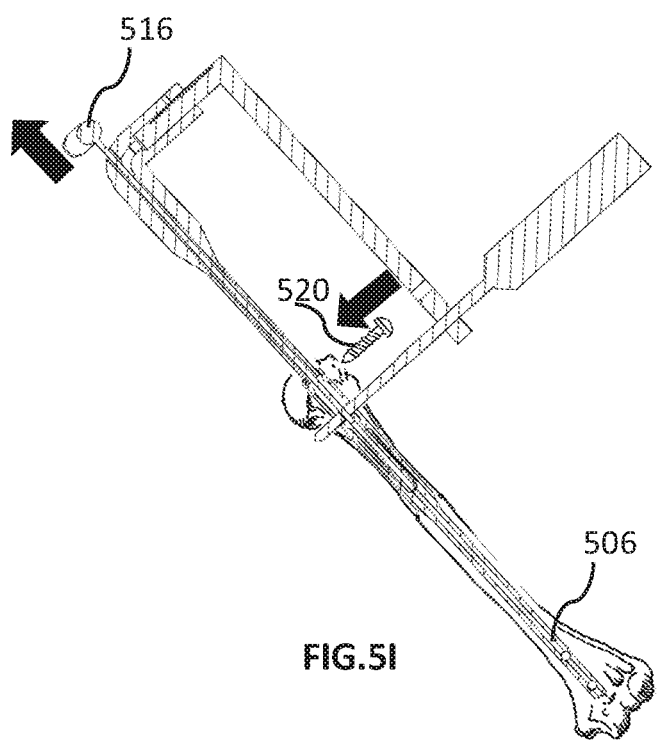

FIG. 5H illustrates tightening the screw mechanism 518 through the hex key 516, causing compression of the fractured bone 502 by bringing the proximal and distal concentric shafts of the rod 506 towards each other.

FIG. 5I illustrates first removing the hex key 516 and then implanting a first proximal fixation screw 520 through a first proximal hole of the rod 506, once a pre-defined compression is achieved. In the context of the present disclosure, the pre-defined compression may be defined by a medical practitioner based on a quality of corresponding bone, and a type of fracture.

Figure 5J:
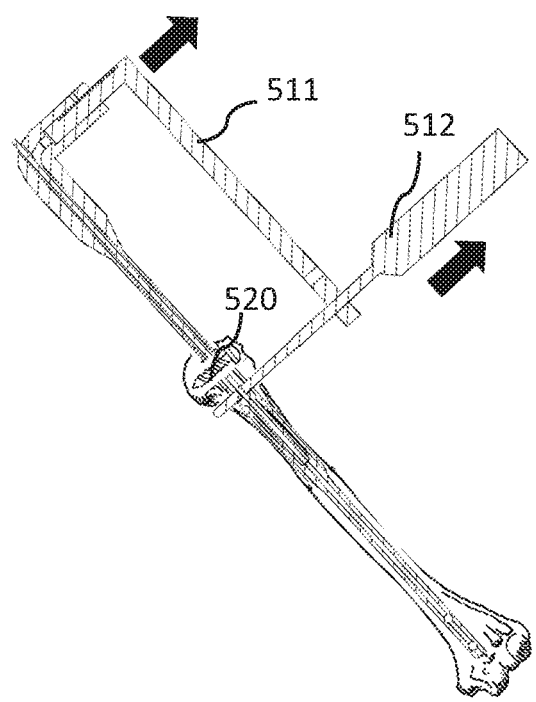

FIG. 5J illustrates first removing the fixation pin 512 and then the arm 511, after implanting the first proximal fixation screw 520.

Figure 5K:
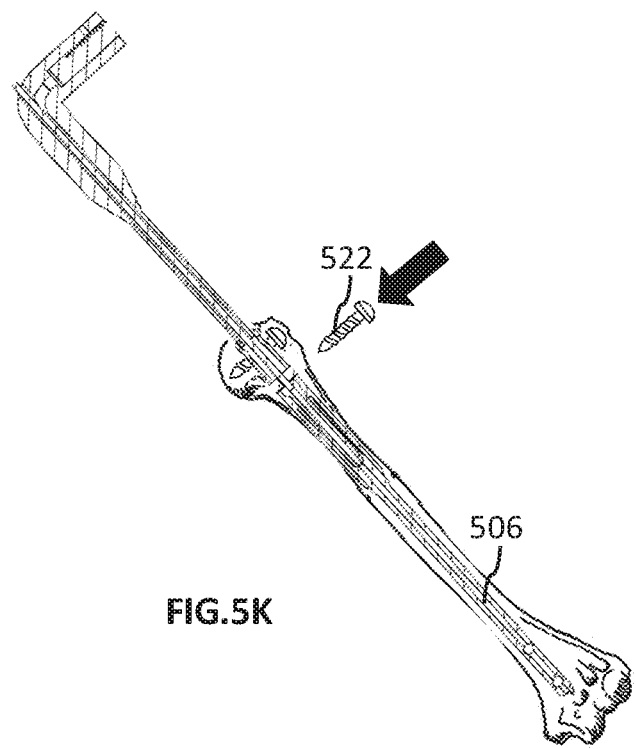

FIG. 5K illustrates implanting a second proximal fixation screw 522 through a second proximal hole of the rod 506, after the fixation pin 512 and the hex key 516 is removed.

Figure 5L:
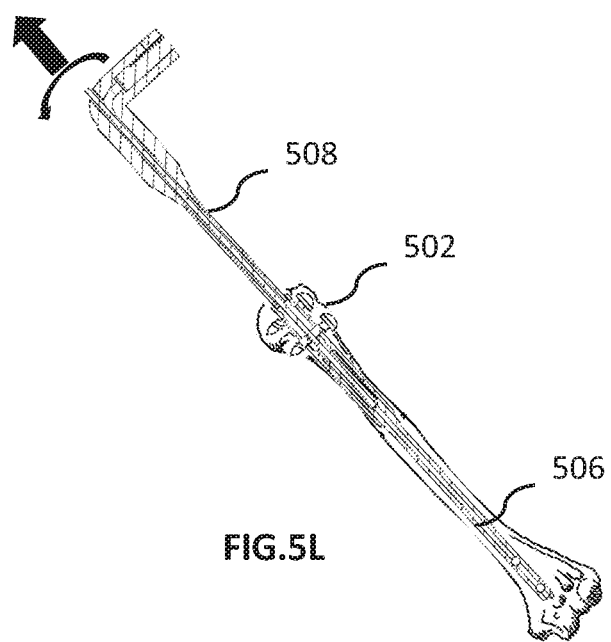

FIG. 5L illustrates removing the deployment arm 508 after the second proximal fixation screw 522 is implanted to form a healed bone 502 in which the fracture is repaired by inserting the compressive intramedullary rod 506.

Modifications to embodiments of the present disclosure described in the foregoing are possible without departing from the scope of the present disclosure as defined by the accompanying claims. Expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A compressive intramedullary rod, comprising:
a first and a second concentric shaft configured to engage with each other in a telescopic manner along a longitudinal axis, through a screw mechanism integrated in the first concentric shaft,
wherein the screw mechanism comprises a bolt in an upper portion for mounting onto the first concentric shaft, and an externally threaded rod in a lower portion for engaging with an internally threaded first channel of the second concentric shaft,
wherein the second concentric shaft includes a second channel extending along corresponding length,
wherein the externally threaded rod includes a third channel extending along corresponding length,
wherein the second channel is aligned with the third channel, when the first and second concentric shafts engage in a telescopic manner upon rotation of the screw mechanism,
wherein the first concentric shaft includes a first set of guide holes disposed in a spaced apart relationship with each other, such that first concentric shaft is configured to be fixed to a proximal fragment of a bone through the first set of guide holes, and
wherein the second concentric shaft includes a second set of guide holes disposed in a spaced apart relationship with each other, such that second concentric shaft is configured to be fixed to a distal fragment of a bone through the second set of guide holes, wherein the first and second set of guide holes are inclined at a differential angle with respect to each other, the differential angle being determined based on an anatomy of the bone to be healed using the compressive intramedullary rod.

2. The compressive intramedullary rod of claim 1, wherein the screw mechanism is referred to as a compressive element, as the screw mechanism is configured to pull the first and second concentric shafts together to create a compression of a bone, once corresponding bone fragments have been fixed to the first and second concentric shafts through respective ones of the first and second guide holes.

3. The compressive intramedullary rod of claim 1, wherein a value of the differential angle is selected from at least one of: 30°, 90° and 150° degrees.

4. The compressive intramedullary rod of claim 1, wherein the first concentric shaft includes a stopping element embedded on an internal surface therein, the stopping element being configured to fit into a groove etched into an outer surface of the second concentric shaft, to prevent dissociation of the first and second concentric shafts during surgical process.

5. The compressive intramedullary rod of claim 1, wherein the bolt fits onto the first concentric shaft through a 45° bevelled surface provided therein.

6. The compressive intramedullary rod of claim 1, wherein alignment of the second and third channels provides a passage for a guide wire that feeds into a fractured bone through the screw mechanism during corresponding implantation process.

7. The compressive intramedullary rod of claim 1, wherein the first concentric shaft and second concentric shaft have one or more internally mated surfaces, wherein distal ends of the one or more internally mated surfaces have a hexagonal cross-section, and wherein proximal ends of the one or more internally mated surfaces have a circular cross-section.

8. A system for fixing a bone fracture in a minimally invasive manner, and for compressing breaks located in a long bone, the system comprising:
a compressive intramedullary rod that comprises:
a first and a second concentric shaft configured to engage with each other in a telescopic manner along a longitudinal axis, through a screw mechanism integrated in the first concentric shaft,
wherein the screw mechanism comprises a bolt in an upper portion for mounting onto the first concentric shaft, and an externally threaded rod in a lower portion for engaging with an internally threaded first channel of the second concentric shaft,
wherein the second concentric shaft includes a second channel extending along corresponding length,
wherein the externally threaded rod includes a third channel extending along corresponding length,
wherein the second channel fully aligns with the third channel, when the first and second concentric shafts engage in a telescopic manner upon rotation of the screw mechanism,
wherein the first concentric shaft includes a first set of guide holes disposed in a spaced apart relationship with each other, such that the first concentric shaft is configured to be fixed to a proximal fragment of a bone through the first set of guide holes, and
wherein the second concentric shaft includes a second set of guide holes disposed in a spaced apart relationship with each other, such that the second concentric shaft is configured to be fixed to a distal fragment of a bone through the second set of guide holes, wherein the first and second set of guide holes are inclined at a differential angle with respect to each other, the differential angle being determined based on an anatomy of the bone to be healed using the compressive intramedullary rod; and
a deployment system for implanting the compressive intramedullary rod in the bone, wherein the deployment system comprises:
a fixation pin having a trocar tip, and a hole that is located adjacent to the trocar trip in a direction perpendicular to a primary axis of the fixation pin,
wherein the fixation pin is configured to insert through a guide hole from the first set of guide holes on the first concentric shaft, to hold the proximal fragment of the bone to a proximal end of the first concentric shaft, while one or more screws inserted through the second set of guide holes are configured to hold a distal end of the second concentric shaft to the distal fragment of the bone;
a hex key configured to insert into the hole of the fixation pin for creating compression between the proximal end of the first concentric shaft and the distal end of the second concentric shaft upon turning, while the screw mechanism is engaged;
a first arm coupled to the hex key for facilitating implant attachment; and
a second arm coupled to the hex key for facilitating alignment of the hole of the fixation pin.

9. The system of claim 8, wherein the screw mechanism is referred to as a compressive element, as the screw mechanism pulls the first and second concentric shafts together to create a compression of a bone, once corresponding bone fragments have been fixed to the first and second concentric shafts through respective ones of the first and second guide holes.

10. The system of claim 8, wherein a value of the differential angle is selected from at least one of: 30°, 90° and 150° degrees.

11. The system of claim 8, wherein the first concentric shaft includes a stopping element embedded on an internal surface therein, the stopping element being configured to fit into a groove etched into an outer surface of the second concentric shaft, to prevent dissociation of the first and second concentric shafts during surgical process.

12. The system of claim 8, wherein the bolt fits onto the first concentric shaft through a 45° bevelled surface provided therein.

13. The system of claim 8, wherein the alignment of the second and third channels provides a passage for a guide wire that feeds into a fractured bone through the screw mechanism during corresponding implantation process.

14. The system of claim 8, wherein the first concentric shaft and second concentric shaft have one or more internally mated surfaces, wherein distal ends of the one or more internally mated surfaces have a hexagonal cross-section, and wherein proximal ends of the one or more internally mated surfaces have a circular cross-section.

15. A deployment system for implanting a compressive intramedullary rod in a bone during a fracture repairing process of the bone, the compressive intramedullary rod comprising first and second concentric shafts configured to engage with each other in a telescopic manner along a longitudinal axis, through a screw mechanism integrated in the first concentric shaft, the deployment system comprising:
    a fixation pin having a trocar tip, and a hole that is located adjacent to the trocar tip in a direction perpendicular to a primary axis of the fixation pin,
    wherein the fixation pin is configured to insert through a guide hole from a first set of guide holes on the first concentric shaft, to hold a proximal fragment of the bone to a proximal end of the first concentric shaft, while one or more screws inserted through a second set of guide holes on the second concentric shaft are configured to hold a distal end of the second concentric shaft to a distal fragment of the bone; and
    a hex key configured to insert into the hole of the fixation pin for creating compression between the proximal end of the first concentric shaft and the distal end of the second concentric shaft upon turning, while the screw mechanism is engaged.

16. The deployment system of claim 15 further comprising a first arm coupled to the hex key for facilitating implant attachment.

17. The deployment system of claim 16 further comprising a second arm coupled to the hex key for facilitating alignment of the hole of the fixation pin.

18. The deployment system of claim 15, wherein the screw mechanism is referred to as a compressive element, as the screw mechanism pulls the first and second concentric shafts together to create a compression of a bone, once corresponding bone fragments have been fixed to the first and second concentric shafts through respective ones of the first and second guide holes.

19. The deployment system of claim 15, wherein the first and second set of guide holes are inclined at a differential angle with respect to each other, and wherein a value of the differential angle is selected from at least one of: 30°, 90° and 150° degrees.

20. A method for implanting a compressive intramedullary rod in a bone during a fracture repairing process of the bone using a deployment device, the compressive intramedullary rod comprising proximal and distal concentric shafts configured to engage with each other in a telescopic manner along a longitudinal axis, through a screw mechanism integrated in the proximal concentric shaft, the proximal and distal concentric shafts including proximal and distal holes respectively, the deployment device having a fixation pin that has a trocar tip, and a key hole that is located adjacent to the trocar trip, and a hex key configured to insert into the key hole of the fixation pin for creating compression between a proximal end of the proximal concentric shaft and a distal end of the distal concentric shaft, the method comprising:
    drilling a hole in the bone;
    positioning a guide wire in the fractured bone such that the guide wire stretches from an opening by incision to a distal most surface in an intramedullary cavity of the bone;
    attaching the compressive intramedullary rod to a deployment arm of the deployment device;
    pushing the compressive intramedullary rod into the fractured bone along a path of the guide wire;
    removing the guide wire;
    attaching the distal concentric shaft to the bone by implanting distal fixation screws through the distal holes of the distal concentric shaft;
    inserting the fixation pin in one of the proximal holes of the proximal concentric shaft;
    inserting the hex key through the key hole in the deployment arm and the fixation pin, such that the hex key interfaces with the screw mechanism;
    tightening the screw mechanism through the hex key, causing compression of the fractured bone;
    removing the hex key once compression is achieved, and a first proximal fixation screw is implanted through a first one of the proximal holes of the proximal concentric shaft; and
    removing the fixation pin, and implanting the second proximal fixation screw through a second one of the proximal holes of the proximal concentric shaft.

* * * * *